(12) United States Patent
Shima et al.

(10) Patent No.: US 11,117,118 B2
(45) Date of Patent: Sep. 14, 2021

(54) HYDROGEN REDUCTION CATALYST FOR CARBON DIOXIDE AND METHOD FOR PRODUCING SAME, HYDROGEN REDUCTION METHOD FOR CARBON DIOXIDE, AND HYDROGEN REDUCTION DEVICE FOR CARBON DIOXIDE

(71) Applicant: Japan Aerospace Exploration Agency, Tokyo (JP)

(72) Inventors: Asuka Shima, Tokyo (JP); Yoshitsugu Sone, Tokyo (JP); Omar Mendoza, Tokyo (JP); Takayuki Abe, Toyama (JP); Mitsuhiro Inoue, Toyama (JP)

(73) Assignee: JAPAN AEROSPACE EXPLORATION AGENCY

( * ) Notice: Subject to any disclaimer, the term of this patent is extended or adjusted under 35 U.S.C. 154(b) by 0 days.

(21) Appl. No.: 16/632,045

(22) PCT Filed: Sep. 7, 2018

(86) PCT No.: PCT/JP2018/033192
§ 371 (c)(1),
(2) Date: Jan. 17, 2020

(87) PCT Pub. No.: WO2019/049983
PCT Pub. Date: Mar. 14, 2019

(65) Prior Publication Data
US 2020/0147589 A1   May 14, 2020

(30) Foreign Application Priority Data
Sep. 7, 2017 (JP) .............................. JP2017-172457

(51) Int. Cl.
| *B01J 23/46* | (2006.01) |
| *B01J 8/06* | (2006.01) |
| *B01J 21/06* | (2006.01) |
| *B01J 35/00* | (2006.01) |
| *B01J 37/34* | (2006.01) |
| *C07C 1/12* | (2006.01) |

(52) U.S. Cl.
CPC ............. *B01J 23/462* (2013.01); *B01J 8/065* (2013.01); *B01J 21/063* (2013.01); *B01J 21/066* (2013.01); *B01J 35/0013* (2013.01); *B01J 37/347* (2013.01); *C07C 1/12* (2013.01); *C07C 2521/06* (2013.01); *C07C 2523/46* (2013.01)

(58) Field of Classification Search
CPC ...... B01J 23/642; B01J 21/063; B01J 21/066; B01J 35/006; C07C 1/12
See application file for complete search history.

(56) References Cited

U.S. PATENT DOCUMENTS

| 4,847,231 A | 7/1989 | Grätzel et al. ................. 502/74 |
| 2007/0213212 A1 | 9/2007 | Abe et al. ................ 502/527.15 |

FOREIGN PATENT DOCUMENTS

| CN | 104148065 A | 11/2014 |
| JP | A-07-116516 | 5/1995 |
| JP | 2005-264297 A | 9/2005 |
| JP | A-2009-131835 | 6/2009 |
| JP | 2013-063405 A | 4/2013 |
| JP | 5392812 B | 1/2014 |

OTHER PUBLICATIONS

JP 2013163675A, machine translation, Jun. 18, 2009.*
International Search Report dated Nov. 20, 2018 in corresponding PCT International Application No. PCT/JP2018/033192.
Written Opinion dated Nov. 20, 2018 in corresponding PCT International Application No. PCT/JP2018/033192.
Jinghua Xu, et al., "$CO_2$ methanation over $TiO_2$-$Al_2O_3$ binary oxides supported Ru catalysts," Chinese Journal of Chemical Engineering, 24 (2016), pp. 140-145.

* cited by examiner

*Primary Examiner* — Jafar F Parsa
(74) *Attorney, Agent, or Firm* — Ostrolenk Faber LLP

(57) ABSTRACT

In a hydrogen reduction catalyst for carbon dioxide of the present invention, catalytic metal nanoparticles and a metal oxide for suppressing grain growth of the catalytic metal nanoparticles are dispersed and supported on a carrier.

8 Claims, 10 Drawing Sheets

(a)

(b)

(a)

(b)

(a)

(b)

(a)

(b)

(a)

(b)

(a)

(b)

HYDROGEN REDUCTION CATALYST FOR CARBON DIOXIDE AND METHOD FOR PRODUCING SAME, HYDROGEN REDUCTION METHOD FOR CARBON DIOXIDE, AND HYDROGEN REDUCTION DEVICE FOR CARBON DIOXIDE

CROSS-REFERENCE TO RELATED APPLICATIONS

The present application is a 35 U.S.C. §§ 371 national phase conversion of PCT/JP2018/033192, filed Sep. 7, 2018, which claims priority to Japanese Patent Application No. 2017-172457, filed Sep. 7, 2017, the contents of which are incorporated herein by reference. The PCT International Application was published in the Japanese language.

TECHNICAL FIELD

The present invention relates to a hydrogen reduction catalyst for carbon dioxide and a method for producing the same. The present invention also relates to a hydrogen reduction method for carbon dioxide and a hydrogen reduction device for carbon dioxide.

BACKGROUND ART

While the application of renewable energy is expected to expand, technologies using renewable energy for generating carriers capable of storing and transporting energy are being actively studied. For example, it has been studied to generate hydrogen by electrolyzing water using renewable energy and to use this as a thermal energy source or fuel for a fuel cell. In addition, the use of hydrogen by converting it to methane or ammonia has also been studied. In particular, methane is expected to be used as an energy carrier since it is a main component of natural gas and the existing infrastructure can be used, which is an advantage.

The Sabatier reaction is known as a technique for converting hydrogen into methane. This Sabatier reaction is a technique in which a catalytic reaction between hydrogen and carbon dioxide produces methane and water. The Sabatier reaction is a reaction in which the reduction rate of carbon dioxide by hydrogen reaches nearly 100% at a temperature of 350° C., and carbon dioxide can be reduced by hydrogen with high efficiency. Further, the Sabatier reaction is an autonomic reaction accompanied by heat generation, and the reaction can be continued without supplying thermal energy or the like from the outside.

As a catalyst for the Sabatier reaction, Patent Document 1 discloses a hydrogen reduction catalyst for carbon dioxide in which at least one type of catalytic metal nanoparticles selected from the group consisting of Fe, Co, Ni, Cu, Ru, Pd, Ag, Ir, and Pt is dispersed and supported on a powdery carrier. 90% or more of the catalytic metal nanoparticles supported on the carrier in the hydrogen reduction catalyst disclosed in Patent Document 1 are fine particles having a particle diameter of 10 nm.

CITATION LIST

Patent Document

[Patent Document 1] Japanese Patent No. 5392812

SUMMARY OF INVENTION

Technical Problem

The hydrogen reduction catalyst for carbon dioxide described in Patent Document 1 in which fine metal nanoparticles are supported is highly active, and by using this catalyst, it becomes possible to efficiently reduce carbon dioxide with hydrogen at a low reaction temperature. However, according to the study by the inventors of the present invention, it has been found that when a hydrogen reduction reaction of carbon dioxide is carried out continuously over a long period of time using a hydrogen reduction catalyst for carbon dioxide supporting only metal nanoparticles, the hydrogen reduction efficiency tends to decrease.

The present invention has been made in view of such circumstances, and has an object of providing a hydrogen reduction catalyst for carbon dioxide by which the hydrogen reduction efficiency is unlikely to decrease even when the hydrogen reduction reaction of carbon dioxide is continuously carried out over a long period of time and a production method thereof, a hydrogen reduction method for carbon dioxide, and an hydrogen reduction device for carbon dioxide.

Solution to Problem

In order to solve the above problems, the hydrogen reduction catalyst for carbon dioxide according to the present invention is characterized in that catalytic metal nanoparticles and a metal oxide for suppressing grain growth of the aforementioned catalytic metal nanoparticles are dispersed and supported on a carrier.

In the hydrogen reduction catalyst for carbon dioxide according to the present invention, the aforementioned catalytic metal nanoparticles may be nanoparticles containing at least one type of metal selected from the group consisting of Fe, Co, Ni, Cu, Ru, Pd, Ag, Ir, and Pt.

Further, in the hydrogen reduction catalyst for carbon dioxide according to the present invention, the aforementioned metal oxide may be nanoparticles containing at least one type of metal oxide selected from the group consisting of titanium dioxide and zirconium dioxide.

Moreover, in the hydrogen reduction catalyst for carbon dioxide according to the present invention, the aforementioned carrier may be a granular material containing at least one type of inorganic material selected from the group consisting of silicon dioxide, magnesium oxide, titanium dioxide, zirconium dioxide, diniobium pentoxide, aluminum oxide, zeolite, and calcium phosphate.

The method for producing a hydrogen reduction catalyst for carbon dioxide according to the present invention is characterized in that sputtering is performed using a target containing a metal and a metal oxide while rolling a carrier, and nanoparticles containing the aforementioned metal and nanoparticles containing the aforementioned metal oxide are dispersed and supported on the surface of the aforementioned carrier.

The hydrogen reduction method for carbon dioxide according to the present invention is characterized by including a step of bringing a gas containing carbon dioxide and hydrogen into contact with the above-mentioned hydrogen reduction catalyst for carbon dioxide.

In the hydrogen reduction method for carbon dioxide according to the present invention, the aforementioned gas containing carbon dioxide and hydrogen may be brought into contact with the aforementioned hydrogen reduction catalyst for carbon dioxide at a temperature of 50° C. or higher and 150° C. or lower.

The hydrogen reduction device for carbon dioxide according to the present invention is characterized by including a reaction tube filled with the hydrogen reduction catalyst for carbon dioxide described above.

Advantageous Effects of Invention

According to the present invention, it is possible to provide a hydrogen reduction catalyst for carbon dioxide by which the catalytic performance is maintained and the hydrogen reduction efficiency is unlikely to decrease even when the hydrogen reduction reaction of carbon dioxide is continuously carried out over a long period of time, and a production method thereof, a hydrogen reduction method for carbon dioxide, and an hydrogen reduction device for carbon dioxide.

DESCRIPTION OF EMBODIMENTS

Figure 1:
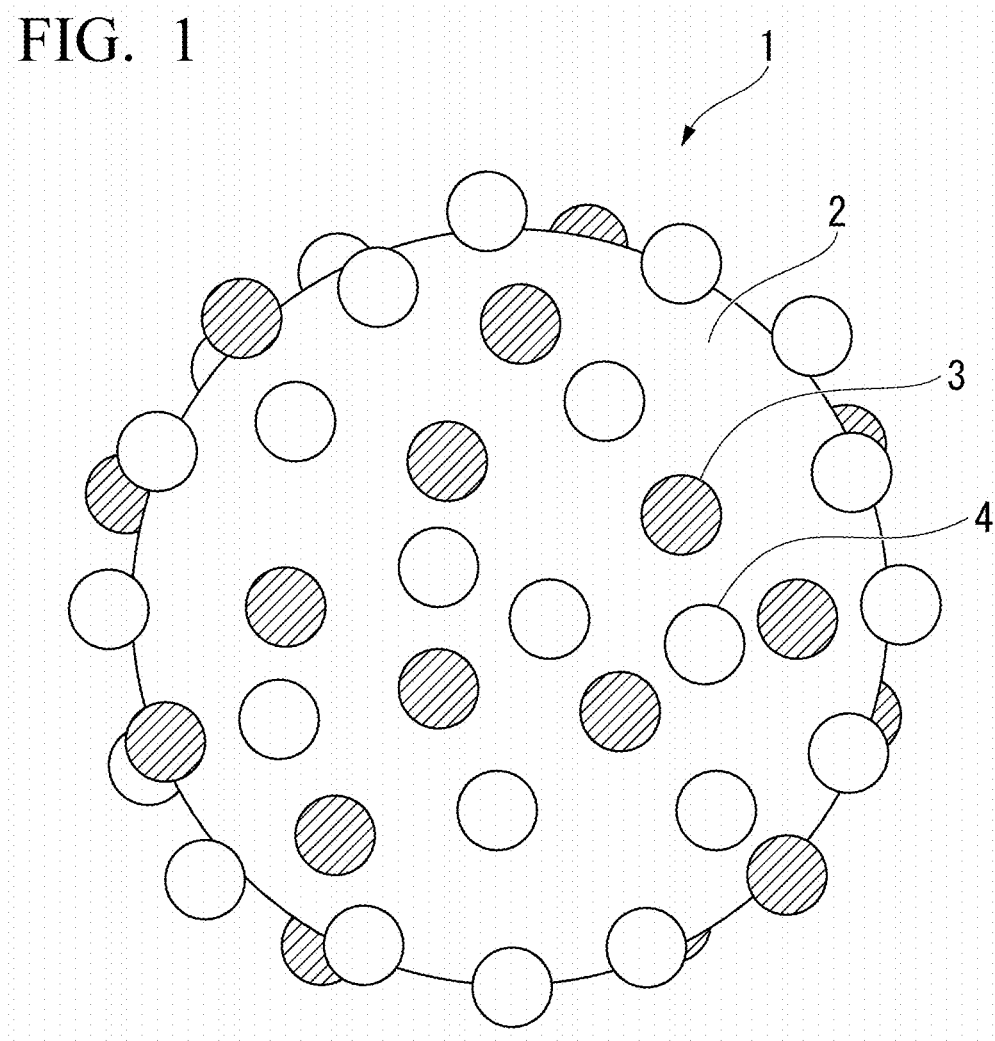
FIG. 1 is an external view schematically showing a structure of a hydrogen reduction catalyst for carbon dioxide according to the present embodiment.

Hereinafter, embodiments of a hydrogen reduction catalyst for carbon dioxide and a production method thereof, a hydrogen reduction method for carbon dioxide, and a hydrogen reduction device for carbon dioxide of the present invention will be described with reference to the accompanying drawings. It should be noted that in the drawings used in the following description, characteristic portions may be shown in an enlarged manner in some cases for the sake of expedience in order to facilitate understanding of the characteristics of the present invention, and the dimensional ratio or the like of each constituent element may be different from that employed in reality.

Further, the present invention is not to be construed as being limited by the following embodiments.

[Hydrogen Reduction Catalyst for Carbon Dioxide]

A hydrogen reduction catalyst for carbon dioxide of the present embodiment is used when producing methane by reacting hydrogen and carbon dioxide using the Sabatier reaction. The reaction process of the hydrogen reduction reaction of carbon dioxide by the Sabatier reaction is considered as follows.

First, as shown in the following reaction formula (1), a carbon dioxide adduct (Me-$CO_{2ad}$) in which carbon dioxide is adsorbed onto a catalytic metal (Me) is generated. When this carbon dioxide adduct is reduced with hydrogen, it changes into a carbon monoxide adduct (Me-$CO_{ad}$) and an oxygen adduct (Me-$O_{ad}$).

Reaction Formula (1):

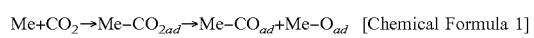

Me+$CO_2$→Me-$CO_{2ad}$→Me-$CO_{ad}$+Me-$O_{ad}$ [Chemical Formula 1]

When the carbon monoxide adduct (Me-$CO_{ad}$) is reduced with hydrogen, it first changes into an aldehyde adduct (Me-$CHO_{ad}$) as shown in the following reaction formula (2). Then, when this aldehyde adduct is further reduced with hydrogen, it changes into a methyl adduct (Me-$CH_{3ad}$), and finally methane is produced. On the other hand, when the oxygen adduct is reduced with hydrogen, water is produced.

Reaction Formula (2)

[Chemical Formula 2]

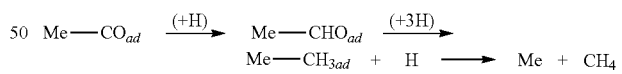

In the Sabatier reaction, the finer the catalytic metal, the higher the activity. Therefore, by using catalytic metal nanoparticles, carbon dioxide can be efficiently reduced with hydrogen at a low reaction temperature. However, according to the study by the inventors of the present invention, it has been found that when the hydrogen reduction reaction of carbon dioxide is carried out using catalytic metal nanoparticles, the catalytic metal nanoparticles aggregate and grow, whereby the hydrogen reduction efficiency tends to decrease. For this reason, in the hydrogen reduction catalyst for carbon dioxide according to the present embodiment, a metal oxide for suppressing grain growth of the catalytic metal nanoparticles is dispersed and supported on the carrier together with the catalytic metal nanoparticles.

FIG. 1 is an external view schematically showing a structure of the hydrogen reduction catalyst for carbon dioxide according to the present embodiment. As shown in FIG. 1, a hydrogen reduction catalyst 1 for carbon dioxide has a structure in which catalytic metal nanoparticles 3 and a metal oxide 4 are dispersed and supported on a carrier 2. It should be noted that in FIG. 1, the metal oxide 4 is dispersed as nanoparticles.

Although there are no particular limitations on the carrier 2, a granular material containing an inorganic material can be used. The carrier 2 is, for example, a granular material containing at least one type of inorganic material selected from the group consisting of silicon dioxide, magnesium oxide, titanium dioxide, zirconium dioxide, diniobium pentoxide, aluminum oxide, zeolite, and calcium phosphate.

The shape of the carrier 2 is spherical in FIG. 1, but is not particularly limited, and may be, for example, a polyhedron shape, an irregular shape, a flake shape, or a scale shape. Further, the average particle diameter of the carrier 2 is not particularly limited, but is, for example, in the range of 0.01 μm or more and 30 μm or less.

The catalytic metal nanoparticles 3 are, for example, nanoparticles containing at least one type of metal selected from the group consisting of Fe, Co, Ni, Cu, Ru, Pd, Ag, Ir and Pt. The catalytic metal nanoparticles 3 may contain a metal oxide as long as the catalytic function is not impaired.

The average particle diameter of the catalytic metal nanoparticles 3 is, for example, in the range of 1 nm or more and 10 nm or less, preferably in the range of 1 nm or more and 5 nm or less, and particularly preferably in the range of 1 nm or more and 3 nm or less. If the average particle diameter of the catalytic metal nanoparticles 3 is too large, there is a possibility that the activity as a catalyst is lowered. On the other hand, if the average particle diameter of the catalytic metal nanoparticles 3 becomes too small, there is a possibility that grains grow easily during the hydrogen reduction reaction of carbon dioxide.

The metal oxide 4 has a function of suppressing the grain growth of the catalytic metal nanoparticles 3. By the catalytic metal nanoparticles 3 and the metal oxide 4 are dispersed and supported, grain growth of the catalytic metal nanoparticles 3 is suppressed. It should be noted that the expression "dispersed and supported" means that each of the catalytic metal nanoparticles 3 and the metal oxide 4 are dispersed on the surface of the carrier 2 without forming an aggregate as shown in FIG. 1. It should be noted that the catalytic metal nanoparticles 3 and the metal oxide 4 being dispersed and supported can be confirmed by the surface observation using a transmission electron microscope (TEM).

The metal oxide 4 is formed of a metal oxide that is not easily changed by heating in the presence of hydrogen and has high reduction resistance. The metal oxide 4 includes, for example, at least one type of metal oxide selected from the group consisting of titanium dioxide and zirconium dioxide. The metal oxide 4 may contain a catalytic metal within a level that the reduction resistance is not impaired. It should be noted that in FIG. 1, the metal oxide 4 is described with the same particle diameter as that of the catalytic metal nanoparticles 3. However, the particle diameter is not particularly limited as long as the metal oxide 4 is supported so that the grain growth of the catalytic metal nanoparticles 3 can be suppressed. Further, the metal oxide 4 may be, for example, in the form of particles or may have an irregular shape.

The amount of the metal oxide 4 dispersed and supported on the carrier 2 is preferably in the range of 5% by mass or more and 50% by mass or less with respect to the mass of the catalytic metal nanoparticles 3. When the amount of the metal oxide 4 is within this range, the catalytic function of the catalytic metal nanoparticles 3 and the function of the metal oxide 4 of suppressing the grain growth of the catalytic metal nanoparticles 3 are exhibited in a balanced manner, and there is a tendency that the hydrogen reduction efficiency is unlikely to decrease even if the hydrogen reduction reaction of carbon dioxide is carried out continuously over a long period of time.

According to the hydrogen reduction catalyst 1 for carbon dioxide of the present embodiment configured as described above, since the catalytic metal nanoparticles 3 and the metal oxide 4 for suppressing the grain growth of the catalyst metal nanoparticles 3 are dispersed and supported on the carrier 2, the catalytic metal nanoparticles 3 are difficult to grow during the hydrogen reduction reaction of carbon dioxide. For this reason, by using the hydrogen reduction catalyst 1 for carbon dioxide according to the present embodiment, even if the hydrogen reduction reaction of carbon dioxide is carried out over a long period of time, the catalytic performance is maintained and the hydrogen reduction efficiency is unlikely to decrease.

[Method for Producing Hydrogen Reduction Catalyst for Carbon Dioxide]

A method for producing a hydrogen reduction catalyst for carbon dioxide according to the present embodiment is a method for producing the hydrogen reduction catalyst 1 for carbon dioxide described above. In the production method of the present embodiment, sputtering is performed using a target containing a metal and a metal oxide while rolling a carrier, and nanoparticles containing the metal and nanoparticles containing the metal oxide are dispersed and supported on the surface of the carrier.

The metal serves as a raw material for the catalytic metal nanoparticles 3 of the hydrogen reduction catalyst 1 for carbon dioxide. The metal is, for example, Fe, Co, Ni, Cu, Ru, Pd, Ag, Ir, or Pt. Although two or more types of these metals may be used in combination, it is preferable to use one of these alone.

The metal oxide serves as a raw material for the metal oxide 4 of the hydrogen reduction catalyst 1 for carbon dioxide. Examples of the metal oxide include titanium dioxide and zirconium dioxide. Each of these metal oxides may be used alone, or two of these may be used in combination.

The carrier serves as a raw material for the carrier 2 of the hydrogen reduction catalyst 1 for carbon dioxide. The carrier is, for example, a granular material containing silicon dioxide, magnesium oxide, titanium dioxide, zirconium dioxide, diniobium pentoxide, zeolite or calcium phosphate. One type of these granular materials may be used alone, or two or more types thereof may be used in combination.

In the production method of the present embodiment, sputtering is performed while rolling the carrier using a target containing the above metal and metal oxide. As an apparatus for performing sputtering while rolling the carrier, for example, a polygonal barrel sputtering apparatus can be used.

Figure 2:
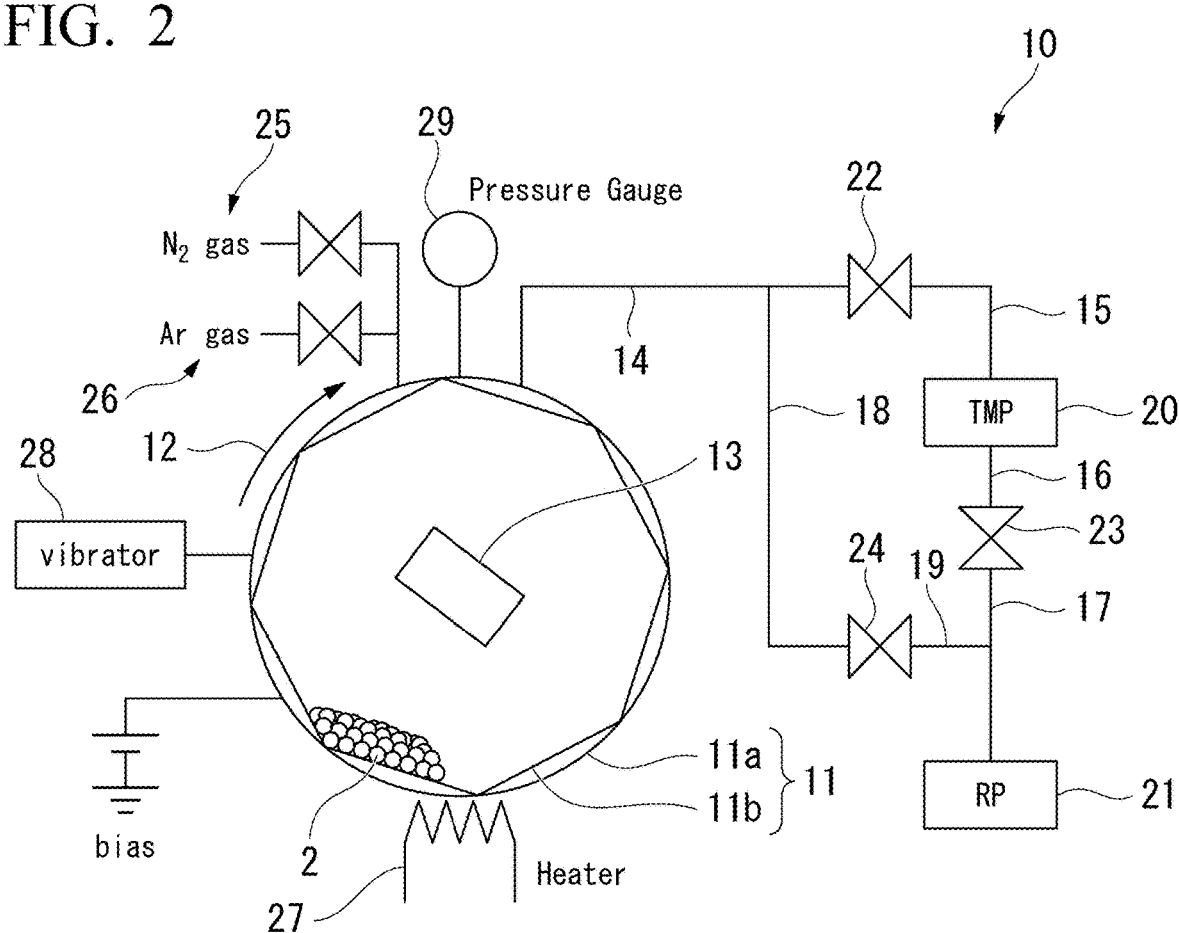
FIG. 2 is a configuration diagram showing an outline of a polygonal barrel sputtering apparatus that can be used in the method for producing a hydrogen reduction catalyst for carbon dioxide according to the present embodiment.
Figure 3:
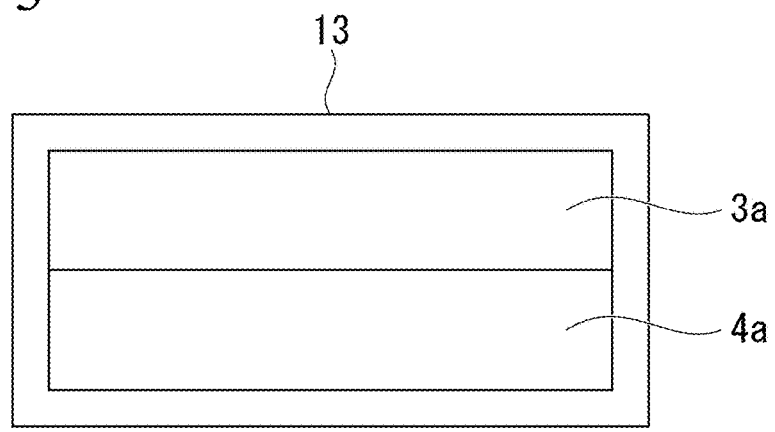
FIG. 3 is a plan view of a target holder of the polygonal barrel sputtering apparatus of FIG. 2.

FIG. 2 is a configuration diagram showing an outline of a polygonal barrel sputtering apparatus that can be used in the method for producing a hydrogen reduction catalyst for carbon dioxide according to the present embodiment, and FIG. 3 is a plan view of a target holder 13 of the polygonal barrel sputtering apparatus of FIG. 2.

As shown in FIG. 2, a polygonal barrel sputtering apparatus 10 includes a vacuum vessel 11 in which the catalytic metal nanoparticles 3 and the metal oxide 4 are dispersed and supported on the carrier 2. The vacuum vessel 11 includes a cylindrical portion 11a and an octagonal barrel 11b installed therein and having an octagonal cross section. The diameter of the cylindrical portion 11a is, for example, 200 mm. The cross section shown here is a cross section substantially parallel to the direction of gravity. It should be noted that in the present embodiment, although the octagonal barrel 11b is used, the present invention is not limited thereto, and a polygonal barrel having a cross section other than an octagonal cross section can also be used.

The vacuum vessel 11 is provided with a rotation mechanism (not shown). By rotating or swinging the octagonal barrel 11b in the direction of an arrow 12 by this rotation mechanism, it becomes possible to perform sputtering while rolling the carrier 2 in the octagonal barrel 11b. The rotation axis when swinging or rotating the octagonal barrel 11b by this rotation mechanism is an axis substantially parallel to the horizontal direction (direction perpendicular to the direction of gravity).

Further, in the vacuum vessel 11, the target holder 13 is arranged on the central axis of the cylinder. As shown in FIG. 3, in the target holder 13, a metal target 3a containing a metal as a raw material for the catalytic metal nanoparticles 3 and a metal oxide target 4a containing a metal oxide as a raw material for the metal oxide 4 are arranged in segments. The area ratio of the sputtering surfaces of the metal target 3a and the metal oxide target 4a is, for example, in the range of 1:0.5 to 1:2. It should be noted that in the present embodiment, although the metal target 3a and the metal oxide target 4a are arranged in segments in the target holder 13, a target in which a metal and a metal oxide are integrated can also be used.

The target holder 13 is configured so that the angle can be freely changed. Because of this, when performing sputtering while swinging or rotating the octagonal barrel 11b, the sputtering surfaces of the metal target 3a and the metal oxide target 4a can be directed in the direction in which the carrier 2 is positioned. As a result, it becomes possible to increase the sputtering efficiency.

One end of a pipe 14 is connected to the vacuum vessel 11, and one side of a first valve 22 is connected to the other end of the pipe 14. One end of a pipe 15 is connected to the other side of the first valve 22, and the other end of the pipe 15 is connected to a suction side of an oil diffusion pump 20. An exhaust side of the oil diffusion pump 20 is connected to one end of a pipe 16, and the other end of the pipe 16 is connected to one side of a second valve 23. The other side of the second valve 23 is connected to one end of a pipe 17, and the other end of the pipe 17 is connected to a pump (RP) 21. Further, the pipe 14 is connected to one end of a pipe 18, and the other end of the pipe 18 is connected to one side of a third valve 24. The other side of the third valve 24 is connected to one end of a pipe 19, and the other end of the pipe 19 is connected to the pipe 17.

This apparatus includes a heater 27 for heating the carrier 2 in the vacuum vessel 11. Further, the present apparatus includes a vibrator 28 for applying vibration to the carrier 2 in the vacuum vessel 11. Moreover, the present apparatus includes a pressure gauge 29 for measuring the internal pressure of the vacuum vessel 11. Furthermore, the present apparatus includes a nitrogen gas introduction mechanism 25 for introducing nitrogen gas into the vacuum vessel 11 and an argon gas introduction mechanism 26 for introducing argon gas into the vacuum vessel 11. In addition, the present apparatus includes a high-frequency application mechanism (not shown) for applying a high frequency between the target (metal target 3a, metal oxide target 4a) and the octagonal barrel 11b.

According to the method for producing a hydrogen reduction catalyst for carbon dioxide of the present embodiment configured as described above, by using a target containing a metal and a metal oxide as a target, the catalytic metal nanoparticles and the metal oxide can be supported at the same time on the surface of the carrier. For this reason, it becomes possible to produce a hydrogen reduction catalyst for carbon dioxide in which fine catalytic metal nanoparticles and metal oxides are respectively highly dispersed and supported. Therefore, the hydrogen reduction catalyst for carbon dioxide produced by the production method of the present embodiment is not only less likely to reduce the hydrogen reduction efficiency, but also capable of realizing a low temperature shift of the reaction temperature of the hydrogen reduction reaction due to further refinement of the catalytic metal nanoparticles.

[Hydrogen Reduction Method for Carbon Dioxide]

The hydrogen reduction method for carbon dioxide of the present embodiment is a method of generating methane and water by hydrogen reduction of carbon dioxide using the Sabatier reaction. The hydrogen reduction method for carbon dioxide of the present embodiment includes a step of bringing a gas containing carbon dioxide and hydrogen into contact with the hydrogen reduction catalyst for carbon dioxide described above.

As a method of bringing a gas containing carbon dioxide and hydrogen into contact with the hydrogen reduction catalyst for carbon dioxide, for example, a method of mixing carbon dioxide and hydrogen in advance and bringing the obtained mixed gas into contact with the hydrogen reduction catalyst for carbon dioxide, or a method of bringing each of carbon dioxide and hydrogen supplied separately from different pipes into contact with a hydrogen reduction catalyst for carbon dioxide can be used. Alternatively, it is also possible to use a method of spraying a hydrogen reduction catalyst for carbon dioxide to a mixed gas of carbon dioxide and hydrogen.

The gas containing carbon dioxide and hydrogen that is brought into contact with the hydrogen reduction catalyst for carbon dioxide may be diluted with an inert gas. As the inert gas, for example, argon can be used. Further, the gas containing carbon dioxide and hydrogen is preferably at a temperature of room temperature to 150° C.

According to the hydrogen reduction method for carbon dioxide of the present embodiment configured as described above, since the above-described hydrogen reduction catalyst for carbon dioxide is used as the reaction catalyst, even if the hydrogen reduction reaction of carbon dioxide is carried out continuously over a long period of time, the catalytic performance is maintained and the hydrogen reduction efficiency is unlikely to decrease.

[Hydrogen Reduction Device for Carbon Dioxide]

The hydrogen reduction device for carbon dioxide according to the present embodiment is an apparatus for generating methane and water by hydrogen reduction of carbon dioxide using the Sabatier reaction. The hydrogen reduction device for carbon dioxide of the present embodiment includes a reaction tube filled with the above-described hydrogen reduction catalyst for carbon dioxide.

Figure 4:
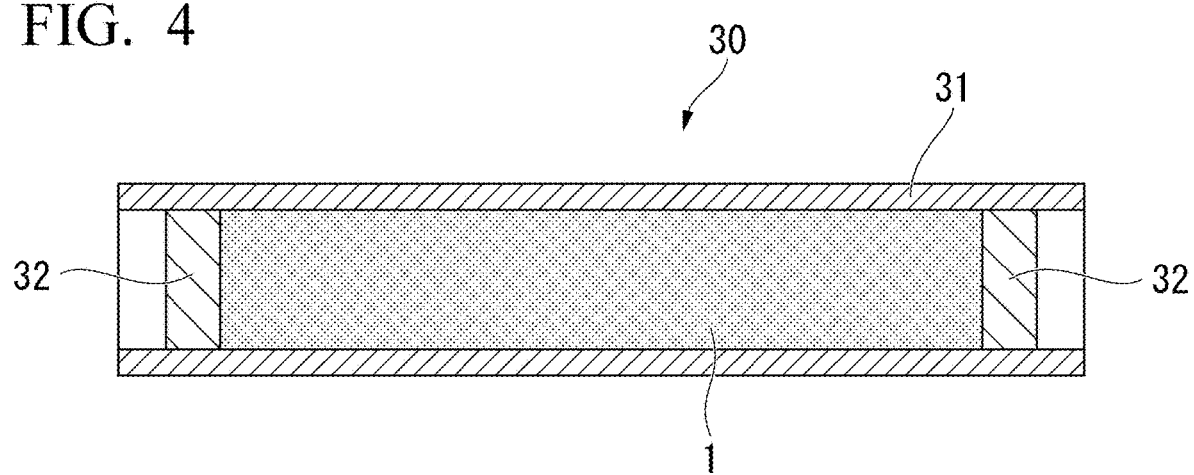
FIG. 4 is a cross-sectional view of a hydrogen reduction device for carbon dioxide according to the present embodiment.

FIG. 4 is a cross-sectional view of a hydrogen reduction device for carbon dioxide according to the present embodiment. As shown in FIG. 4, a hydrogen reduction device 30 for carbon dioxide includes a reaction tube 31 in which both ends are opened, a hydrogen reduction catalyst 1 for carbon dioxide filled in the reaction tube 31, and porous bodies 32 arranged in the vicinity of openings at both ends of the reaction tube 31.

The shape of the reaction tube 31 is not particularly limited, and can be formed into, for example, a cylindrical shape, an elliptical cylindrical shape, or a polygonal cylindrical shape. The material of the reaction tube 31 is not particularly limited as long as it is not reactive with carbon dioxide and hydrogen as raw materials and methane and water as reaction products. As a material of the reaction tube 31, for example, plastic, metals, ceramics, glass or the like can be used.

The porous bodies 32 allow gas such as carbon dioxide, hydrogen, methane and water (water vapor) to pass through without passing through the hydrogen reduction catalyst 1 for carbon dioxide. As the porous bodies 32, for example, a metal fiber filter, a ceramic filter, a glass filter, a foam metal, or glass wool can be used.

The hydrogen reduction catalyst 1 for carbon dioxide may be filled in the reaction tube 31 in a state of being dispersed and attached in a porous substrate. By dispersing and attaching the hydrogen reduction catalyst 1 for carbon dioxide to the porous substrate, a gas flow path in the reaction tube 31 can be secured, and the pressure loss of the gas can be reduced. As the porous substrate, for example, a metal fiber filter, a ceramic filter, a glass filter, a foam metal, or glass wool can be used.

Further, the hydrogen reduction catalyst 1 for carbon dioxide may be filled in the reaction tube 31 in a state of being formed into a porous shape. By making the hydrogen reduction catalyst 1 for carbon dioxide porous, a gas flow path in the reaction tube 31 can be secured, and the pressure loss of the gas can be reduced. For example, a pressing method can be used as a method for forming a porous shape.

According to the hydrogen reduction device 30 for carbon dioxide of the present embodiment configured as described above, since the above-described hydrogen reduction catalyst 1 for carbon dioxide is filled as a reaction catalyst, even if the hydrogen reduction reaction of carbon dioxide is carried out continuously over a long period of time, the catalytic performance is maintained and the hydrogen reduction efficiency is unlikely to decrease.

EXAMPLES

Next, the present invention will be described with reference to examples.

Example 1

Using the polygonal barrel sputtering apparatus 10 shown in FIG. 2, a $TiO_2$ granular material supporting Ru—$TiO_2$ was prepared in which Ru nanoparticles and $TiO_2$ nanoparticles were dispersed and supported on a $TiO_2$ granular material.

More specifically, first, a Ru target as the metal target 3a and a $TiO_2$ target as the metal oxide target 4a were placed in the target holder 13 of the polygonal barrel sputtering apparatus 10. The area ratio of the sputtering surfaces of the Ru target and the $TiO_2$ target placed in the target holder 13 was 1:1.

Example 1

Using the polygonal barrel sputtering apparatus 10 shown in FIG. 2, a $TiO_2$ granular material supporting Ru—$TiO_2$ was prepared in which Ru nanoparticles and $TiO_2$ nanoparticles were dispersed and supported on a $TiO_2$ granular material.

More specifically, first, a Ru target as the metal target 3a and a $TiO_2$ target as the metal oxide target 4a were placed in the target holder 13 of the polygonal barrel sputtering apparatus 10. The area ratio of the sputtering surfaces of the Ru target and the $TiO_2$ target placed in the target holder 13 was 1:1.

Subsequently, the pressure inside the octagonal barrel 11b was reduced to $8.0 \times 10^{-4}$ Pa or less using the oil diffusion pump 20. Thereafter, Ar gas was introduced into the octagonal barrel 11b by the argon gas introduction mechanism 26, and the pressure inside the octagonal barrel 11b was set to 0.8 Pa. Then, the octagonal barrel 11b was swung by the rotation mechanism at an angle of 75° and 4.3 rpm to roll the $TiO_2$ powder in the octagonal barrel 11b. At that time, the target holder 13 was tilted so that the sputtering surfaces of the Ru target and the $TiO_2$ target faced downward. Thereafter, a high frequency of 100 W was applied to the high frequency application mechanism (RF oscillator) for 4 hours while swinging the octagonal barrel 11b to obtain a $TiO_2$ granular material supporting Ru—$TiO_2$ (Ru—$TiO_2$/$TiO_2$).

The surface of the produced Ru—$TiO_2$/$TiO_2$ was observed with a TEM. In addition, about 100 Ru particles represented by black spots on the TEM photograph were arbitrarily selected, and the average particle diameter of the Ru nanoparticles was calculated by actual measurement from the enlarged photograph.

A TEM photograph of Ru—$TiO_2$/$TiO_2$ is shown in (a) of HG 5, and a particle size distribution diagram of Ru nanoparticles is shown in (b). From the TEM photograph of FIG. 5 (a), it was confirmed that fine Ru nanoparticles were highly dispersed on the surface of Ru—$TiO_2$/$TiO_2$. In addition, the average particle diameter (average value of 132 particles) of the Ru nanoparticles calculated from the particle size distribution diagram of FIG. 5 (b) was as very fine as 1.7 nm.

Example 2

A $TiO_2$ granular material supporting Ru—$ZrO_2$ (Ru—$ZrO_2$/$TiO_2$) was prepared in which Ru nanoparticles and $ZrO_2$ nanoparticles were dispersed and supported on a $TiO_2$ granular material in the same manner as in Example 1, except that a $ZrO_2$ target was used instead of the $TiO_2$ target in the target holder 13 of the polygonal barrel sputtering apparatus 10, and the Ru target and the $ZrO_2$ target were placed in the target holder 13 so that the area ratio of the sputtering surfaces was 1:0.5.

Figure 6:
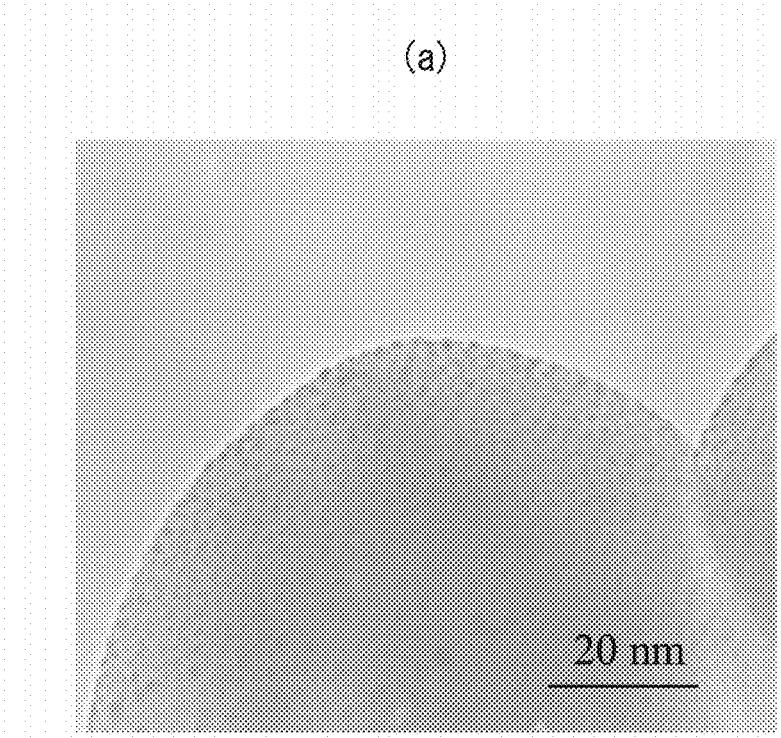
FIG. 6 (a) is a TEM photograph immediately after the production of a hydrogen reduction catalyst for carbon dioxide (Ru—$ZrO_2$/$TiO_2$) produced in Example 2, and (b) is a particle size distribution diagram of Ru nanoparticles supported on the Ru—$ZrO_2$/$TiO_2$.
Figure 6:
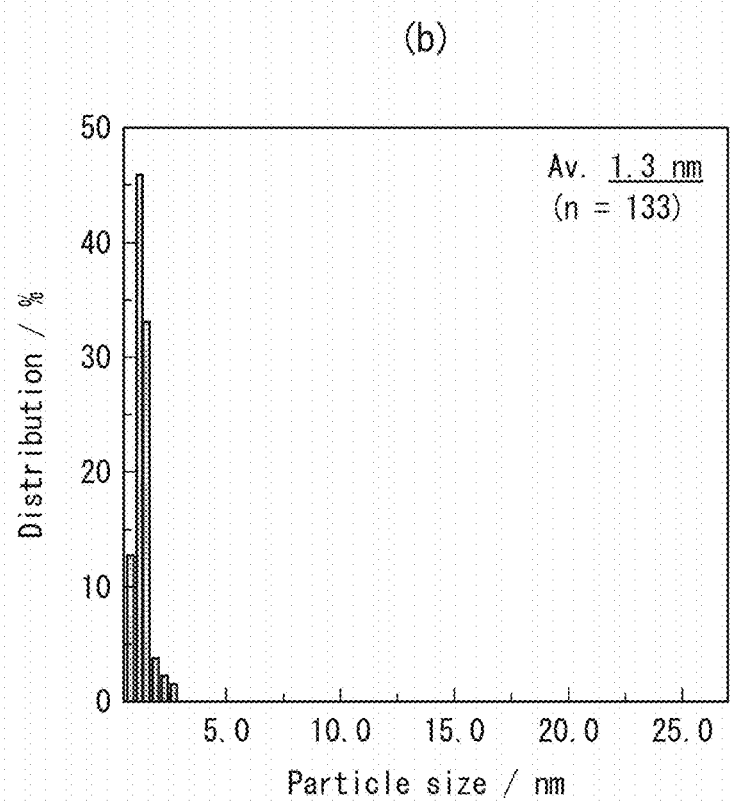

A TEM photograph of the produced Ru—$ZrO_2$/$TiO_2$ is shown in (a) of FIG. 6, and a particle size distribution diagram of Ru nanoparticles is shown in (b). From the TEM photograph of FIG. 6 (a), it was confirmed that fine Ru nanoparticles were highly dispersed on the surface of Ru—$ZrO_2$/$TiO_2$. In addition, the average particle diameter (average value of 133 particles) of the Ru nanoparticles calculated from the particle size distribution diagram of FIG. 6 (b) was as very fine as 1.3 nm.

Comparative Example 1

A $TiO_2$ granular material supporting Ru (Ru/$TiO_2$) was prepared in which Ru nanoparticles were supported on a $TiO_2$ granular material in the same manner as in Example 1, except that only the Ru target is placed without placing the $TiO_2$ target in the target holder of the polygonal barrel sputtering apparatus, and the application time of high frequency to the high-frequency application mechanism was set to 2 hours.

Figure 7:
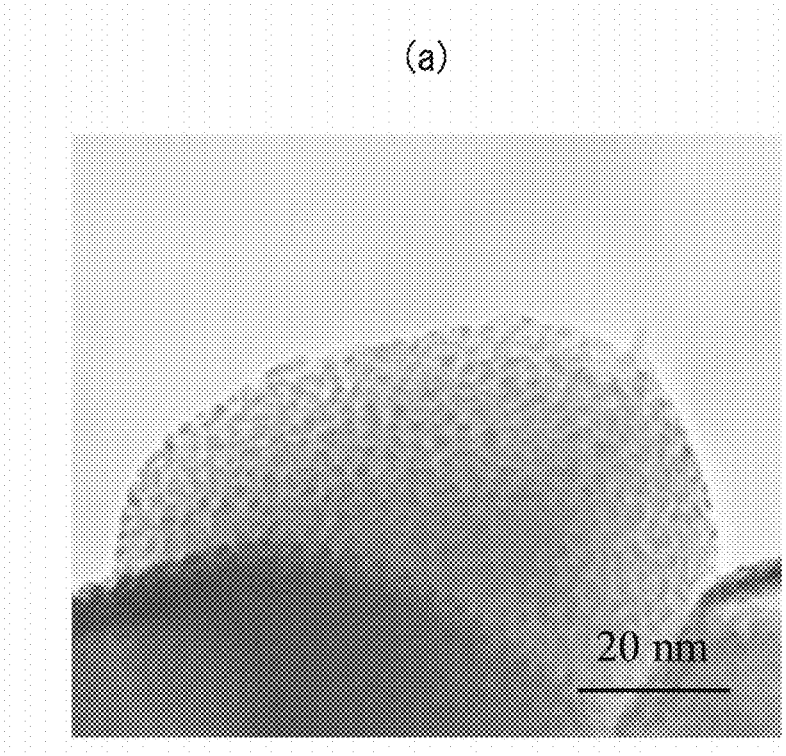
FIG. 7 (a) is a TEM photograph immediately after the production of a hydrogen reduction catalyst for carbon dioxide (Ru/$TiO_2$) produced in Comparative Example 1, and (b) is a particle size distribution diagram of Ru nanoparticles supported on the Ru/$TiO_2$.
Figure 7:
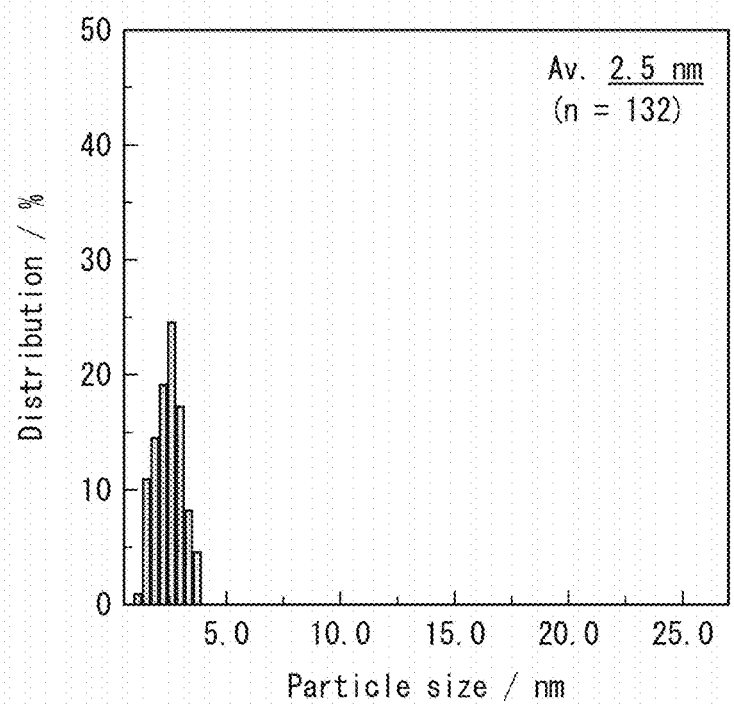

A TEM photograph of the produced Ru/TiO$_2$ is shown in (a) of FIG. 7, and a particle size distribution diagram of Ru nanoparticles is shown in (b). From the TEM photograph of FIG. 7 (a), it was confirmed that Ru nanoparticles were highly dispersed on the surface of Ru/TiO$_2$. The average particle diameter (average value of 132 particles) of the Ru nanoparticles calculated from the particle size distribution particle size distribution diagram of FIG. 7 (b) was 2.5 nm, which was slightly larger than those produced in Examples 1 and 2.

[Evaluation]

For the catalysts for hydrogen reduction of carbon dioxide produced in Examples 1 and 2 and Comparative Example 1, the temperature dependence of the carbon dioxide reduction rate was measured. Subsequently, the surface state of the hydrogen reduction catalyst for carbon dioxide used in the temperature dependence measurement was evaluated.

(Measurement of Temperature Dependence)

1.0 g of a hydrogen reduction catalyst for carbon dioxide as a sample and 2.0 g of glass wool were mixed to obtain glass wool with a catalyst in which the hydrogen reduction catalyst was dispersed and attached in the glass wool. The obtained glass wool with a catalyst was filled in a glass tube (made of borosilicate glass, diameter: 20 mm) having an opening in the vertical direction and provided with a glass filter at the bottom so that the height was 30 mm Thermocouples were placed at three locations: at positions 5 mm respectively from the upper and lower ends of the filled glass wool with a catalyst; and at the center. A glass tube filled with the glass wool with a catalyst was placed on a heater, the upper opening of the glass tube was connected to a gas supply pipe equipped with a mass flowmeter (MFC), and the lower opening was connected to an exhaust pipe.

Subsequently, CO$_2$ gas and H$_2$ gas were supplied from the gas supply pipe to the glass tube under the conditions of a flow rate of 10 mL/min and a flow rate of 40 mL/min (GHSV: 318 h−1, WHSV: 3,000 mL/g·h), respectively. After setting the temperature of the heater to 160° C., and confirming that the temperatures of the glass wool with a catalyst measured by the respective thermocouples placed at three locations were respectively kept constant for 30 minutes or more, the composition of the gas discharged from the exhaust pipe was analyzed using gas chromatography, and the yield of CH$_4$ produced by the CO$_2$ reduction reaction (reduction rate of carbon dioxide) was calculated. This operation was performed by increasing the temperature of the heater in stages by 20° C. until the temperature of the heater reached 240° C. It should be noted that the temperature of the heater was controlled by a PID controller. The results are shown in FIG. 8 as a graph in which the horizontal axis denotes the maximum temperature of catalyst which is the highest value among the average values during sampling of the respective thermocouples placed at the three locations described above, and the vertical axis denotes the reduction rate of carbon dioxide.

Figure 8:
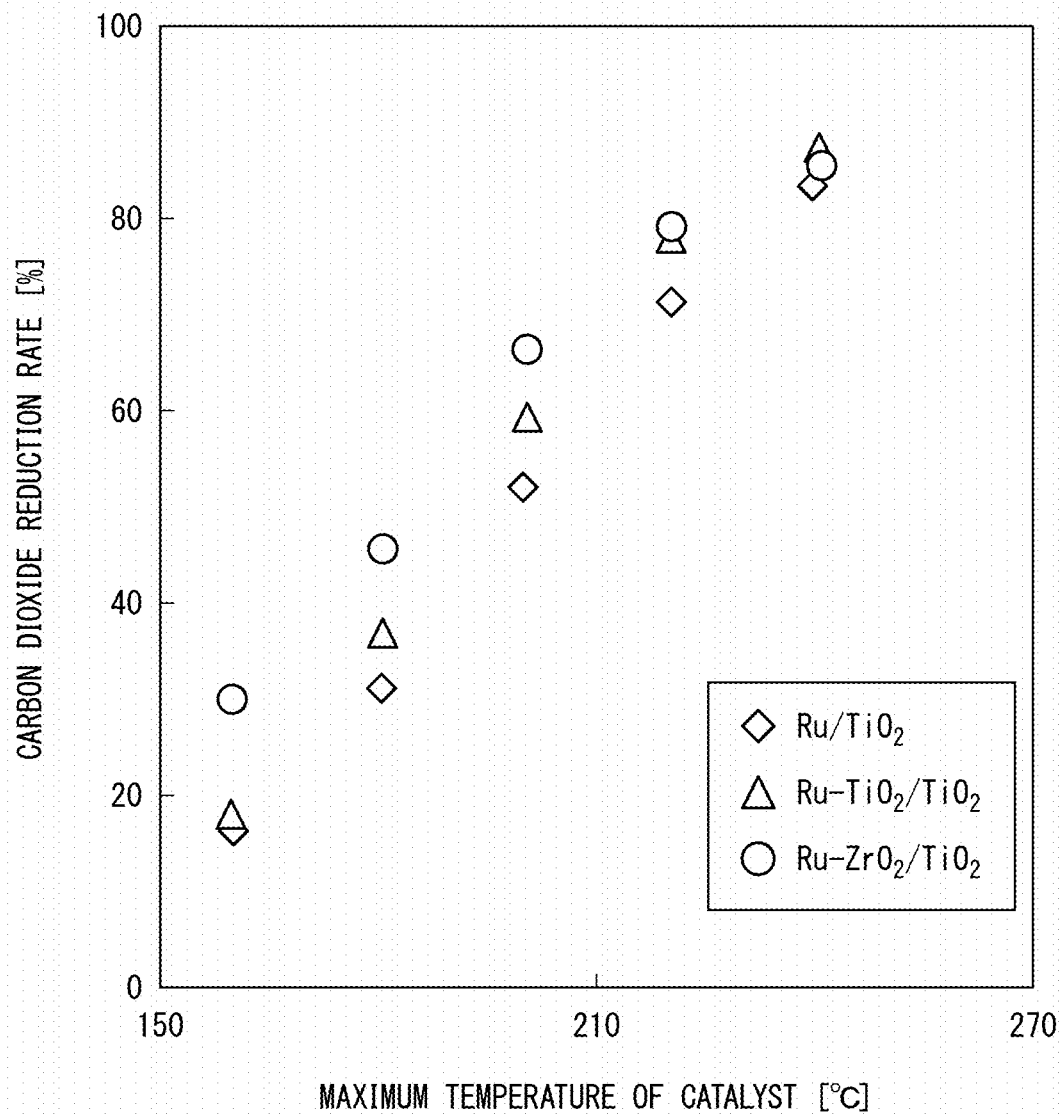
FIG. 8 is a graph showing the results of evaluating the temperature dependence of carbon dioxide reduction rates of the hydrogen reduction catalyst for carbon dioxide produced in Examples 1 and 2 and Comparative Example 1.

From the graph of FIG. 8, it was confirmed that the hydrogen reduction catalysts for carbon dioxide produced in Example 1 and Example 2 increased the reduction rate of carbon dioxide at a lower temperature than that produced in Comparative Example 1, and exhibited a high reduction rate at any temperature. It is thought that this is because the hydrogen reduction catalysts for carbon dioxide of Example 1 and Example 2 have a smaller average particle diameter of Ru nanoparticles than that of Comparative Example 1.

(Evaluation of Surface Condition of Hydrogen Reduction Catalyst for Carbon Dioxide)

The glass wool with a catalyst used in the above temperature dependence measurement was taken out from the glass tube. Subsequently, the hydrogen reduction catalyst for carbon dioxide attached to the glass wool was recovered, the surface state of the hydrogen reduction catalyst was observed using a TEM, and the particle size distribution of Ru particles was measured.

Figure 9:
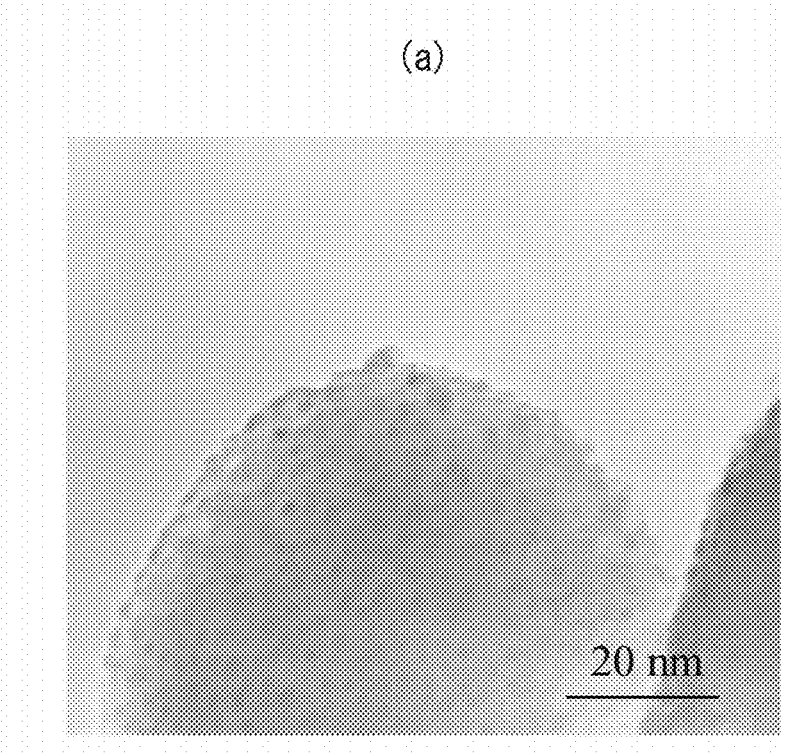
FIG. 9 (a) is a TEM photograph after use of the hydrogen reduction catalyst for carbon dioxide (Ru—$TiO_2$/$TiO_2$) produced in Example 1, and (b) is a particle size distribution diagram of Ru nanoparticles supported on the Ru—$TiO_2$/$TiO_2$.
Figure 9:
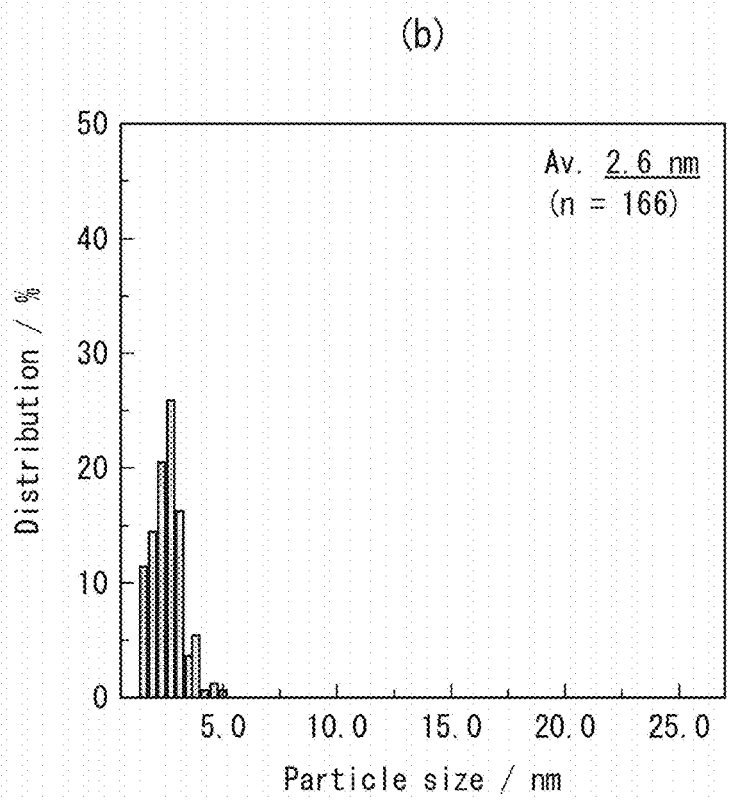

FIG. 9 (a) is a TEM photograph after use of the hydrogen reduction catalyst for carbon dioxide (Ru—TiO$_2$/TiO$_2$) produced in Example 1, and (b) is a particle size distribution diagram of Ru nanoparticles supported on the Ru—TiO$_2$/TiO$_2$.

Figure 5:
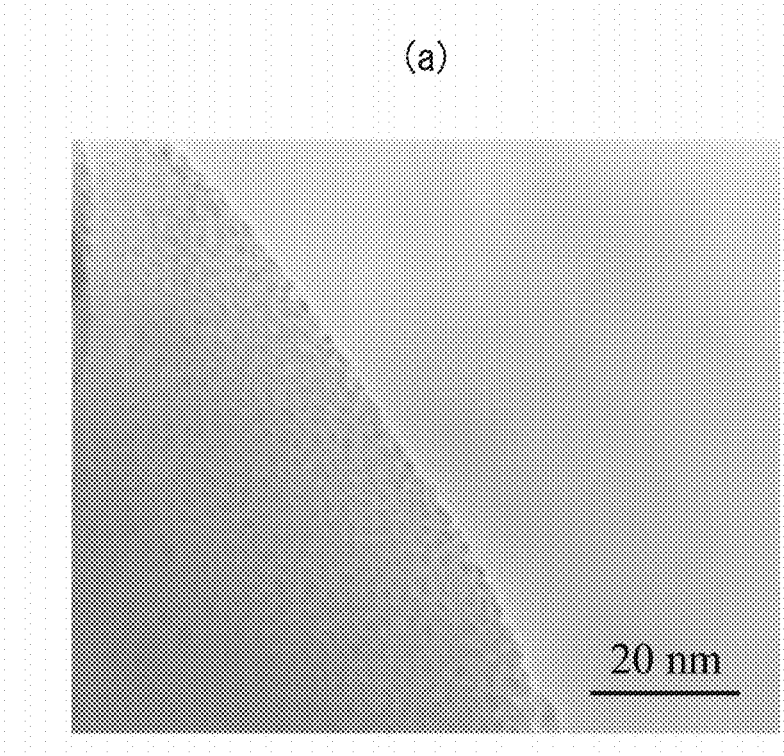
FIG. 5 (a) is a TEM photograph immediately after the production of a hydrogen reduction catalyst for carbon dioxide (Ru—$TiO_2$/$TiO_2$) produced in Example 1, and (b) is a particle size distribution diagram of Ru nanoparticles supported on the Ru—$TiO_2$/$TiO_2$.
Figure 5:
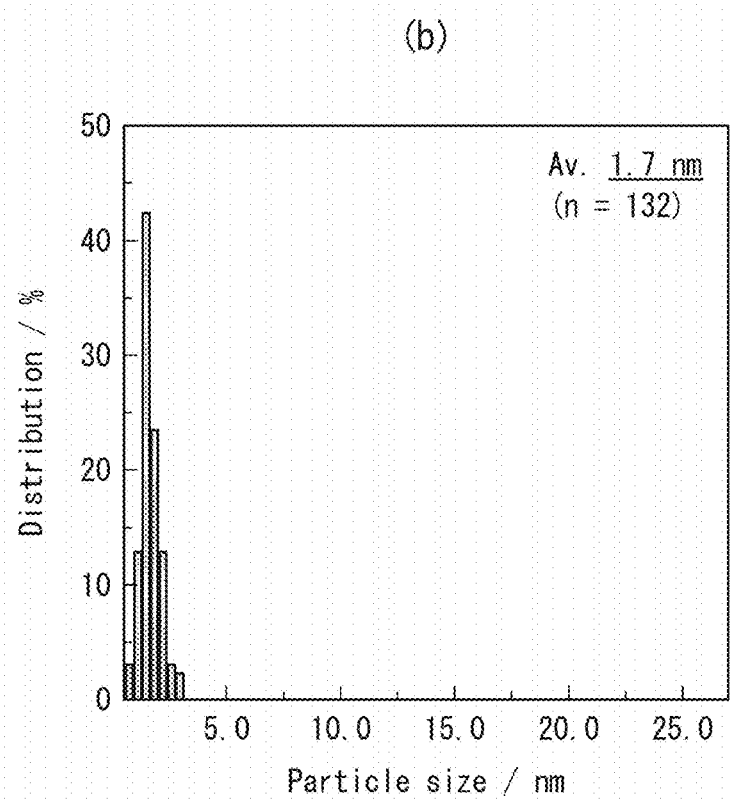

By comparing the TEM photograph of FIG. 9 (a) with the TEM photograph of FIG. 5 (a), overall uniform grain growth of Ru nanoparticles was confirmed in the Ru—TiO$_2$/TiO$_2$ after use. Moreover, the average particle diameter (average value of 166 particles) of the Ru nanoparticles calculated from the particle size distribution diagram of FIG. 9 (b) was 2.6 nm.

Figure 10:
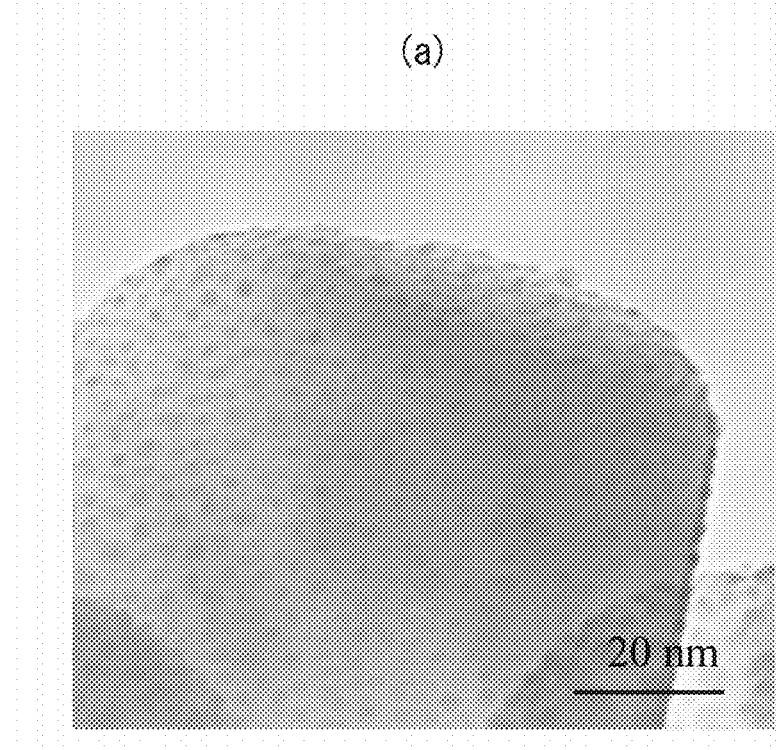
FIG. 10 (a) is a TEM photograph after use of the hydrogen reduction catalyst for carbon dioxide (Ru—$ZrO_2$/$TiO_2$) produced in Example 2, and (b) is a particle size distribution diagram of Ru nanoparticles supported on the Ru—$ZrO_2$/$TiO_2$.
Figure 10:
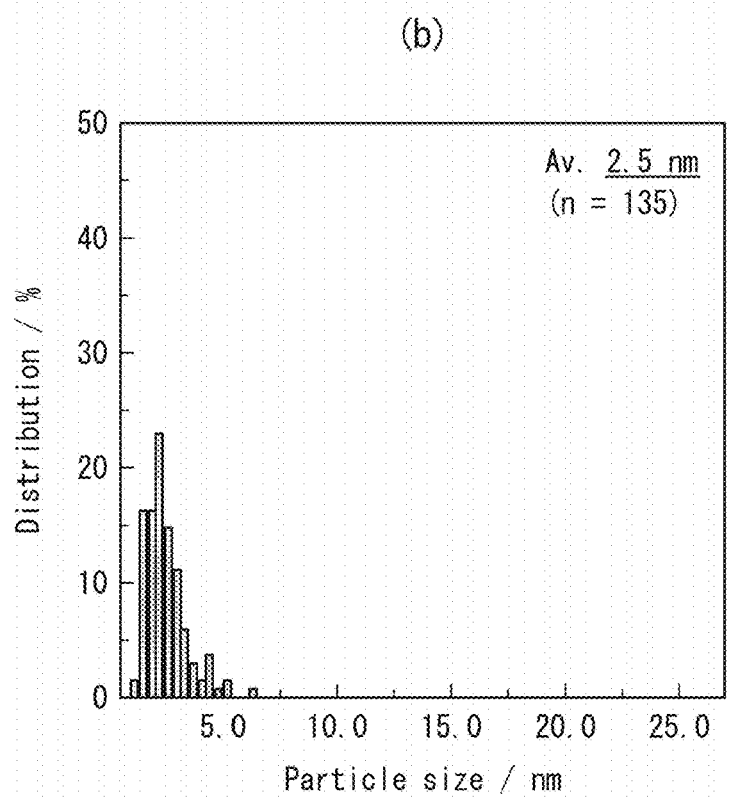

FIG. 10 (a) is a TEM photograph after use of the hydrogen reduction catalyst for carbon dioxide (Ru—ZrO$_2$/TiO$_2$) produced in Example 2, and (b) is a particle size distribution diagram of Ru nanoparticles supported on the Ru—ZrO$_2$/TiO$_2$.

By comparing the TEM photograph of FIG. 10 (a) with the TEM photograph of FIG. 6 (a), overall uniform grain growth of Ru nanoparticles was confirmed in the Ru—ZrO$_2$/TiO$_2$ after use. Moreover, the average particle diameter (average value of 135 particles) of the Ru nanoparticles calculated from the particle size distribution diagram of FIG. 9 (b) was 2.5 nm.

Figure 11:
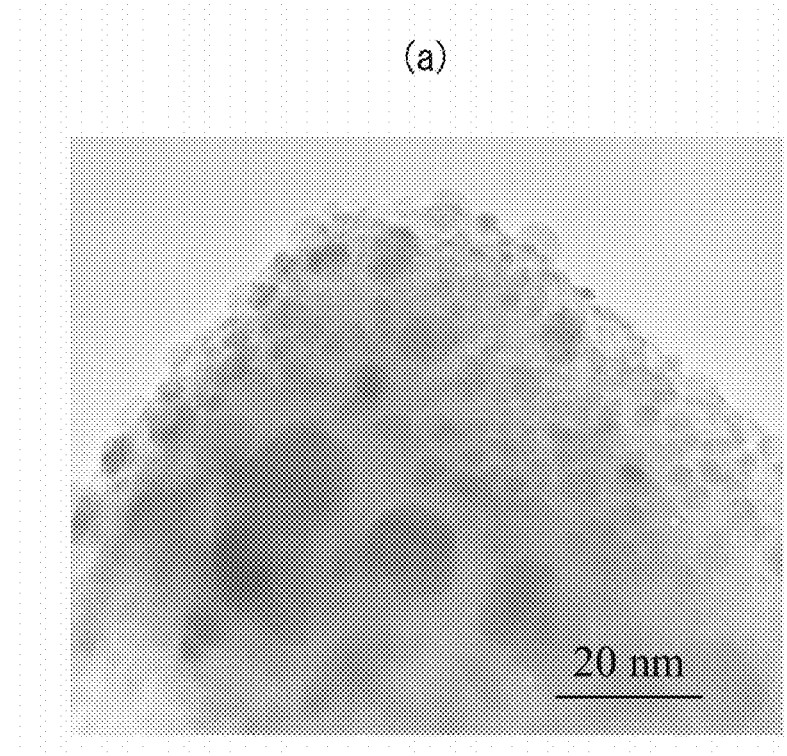
FIG. 11 (a) is a TEM photograph after use of the hydrogen reduction catalyst for carbon dioxide (Ru/$TiO_2$) produced in Comparative Example 1, and (b) is a particle size distribution diagram of Ru nanoparticles supported on the Ru/$TiO_2$.
Figure 11:
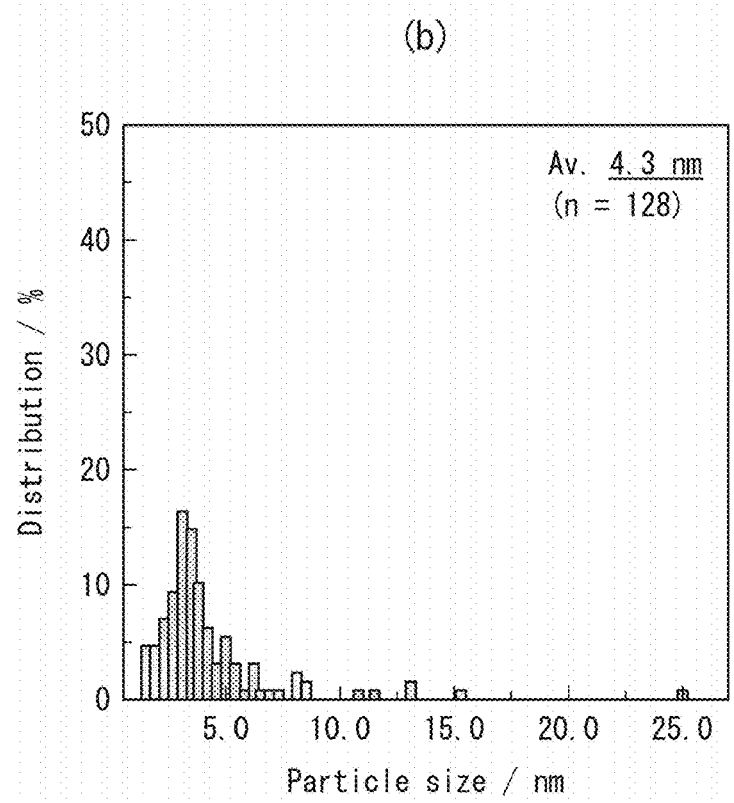

FIG. 11 (a) is a TEM photograph after use of the hydrogen reduction catalyst for carbon dioxide (Ru/TiO$_2$) produced in Comparative Example 1, and (b) is a particle size distribution diagram of Ru nanoparticles supported on the Ru/TiO$_2$.

By comparing the TEM photograph of FIG. 11 (a) with the TEM photograph of FIG. 7 (a), nonuniform grain growth of Ru nanoparticles and generation of large particles having a major axis larger than 20 nm were confirmed in the Ru/TiO$_2$ after use. In addition, the average particle diameter (average value of 128 particles) of the Ru nanoparticles calculated from the particle size distribution diagram of FIG. 9 (b) was 4.3 nm.

From the above results, it was confirmed that according to the present example, it is possible to produce a hydrogen reduction catalyst for carbon dioxide in which fine Ru nanoparticles and metal oxide are highly dispersed and supported. Further, it was confirmed that by using this hydrogen reduction catalyst for carbon dioxide, the hydrogen reduction reaction temperature of carbon dioxide can be further lowered, and the Ru nanoparticles are difficult to grow even if the hydrogen reduction reaction of carbon dioxide is carried out continuously over a long period of time.

REFERENCE SIGNS LIST

1 Hydrogen reduction catalyst for carbon dioxide
2 Carrier
3 Catalytic metal nanoparticle
4 Metal oxide
10 Polygonal barrel sputtering apparatus
11 Vacuum vessel
11a Cylindrical portion
11b Octagonal barrel 12 Arrow
13 Target holder
14, 15, 16, 17, 18, 19 Pipe
20 Oil diffusion pump
21 Pump (RP)
22 First valve
23 Second valve
24 Third valve
25 Nitrogen gas introduction mechanism
26 Argon gas introduction mechanism
27 Heater
28 Vibrator
29 Pressure gauge
30 Hydrogen reduction device for carbon dioxide
31 Reaction tube
32 Porous body

The invention claimed is:

1. A hydrogen reduction catalyst for carbon dioxide in which catalytic metal nanoparticles and a metal oxide for suppressing grain growth of said catalytic metal nanoparticles are dispersed and supported on a carrier,
wherein the carrier is a granular material containing at least one type of inorganic material, and the catalytic metal nanoparticles and the metal oxide are dispersed and supported on the carrier containing the inorganic material,
wherein each of the catalytic metal nanoparticles and the metal oxide are dispersed on the surface of the carrier without forming an aggregate, and
wherein the hydrogen reduction catalyst is produced by sputtering being performed using a target containing a metal and a metal oxide.

2. The hydrogen reduction catalyst for carbon dioxide according to claim 1, wherein said catalytic metal nanoparticles are nanoparticles containing at least one type of metal selected from the group consisting of Fe, Co, Ni, Cu, Ru, Pd, Ag, Ir, and Pt.

3. The hydrogen reduction catalyst for carbon dioxide according to claim 1, wherein said metal oxide is at least one type of metal oxide selected from the group consisting of titanium dioxide and zirconium dioxide.

4. The hydrogen reduction catalyst for carbon dioxide according to claim 1,
wherein the inorganic material contained in the granular material is at least one type of inorganic material selected from the group consisting of silicon dioxide, magnesium oxide, titanium dioxide, zirconium dioxide, diniobium pentoxide, aluminum oxide, zeolite, and calcium phosphate.

5. A method for producing a hydrogen reduction catalyst for carbon dioxide, wherein sputtering is performed using a target containing a metal and a metal oxide while rolling a carrier, and nanoparticles containing said metal and said metal oxide are dispersed and supported on a surface of said carrier,
wherein the carrier is a granular material containing at least one type of inorganic material, and the nanoparticles of the metal which is a catalytic metal and the metal oxide are dispersed and supported on the carrier containing the inorganic material, and
wherein each of the catalytic metal nanoparticles and the metal oxide are dispersed on the surface of the carrier without forming an aggregate.

6. A hydrogen reduction method for carbon dioxide, the method comprising a step of bringing a gas containing carbon dioxide and hydrogen into contact with the hydrogen reduction catalyst for carbon dioxide according to claim 1.

7. The hydrogen reduction method for carbon dioxide according to claim 6, wherein said gas containing carbon dioxide and hydrogen is brought into contact with said hydrogen reduction catalyst for carbon dioxide at a temperature of 50° C. or higher and 150° C. or lower.

8. A hydrogen reduction device for carbon dioxide comprising a reaction tube filled with the hydrogen reduction catalyst for carbon dioxide according to claim 1.

* * * * *